United States Patent
Flammang

(10) Patent No.: US 6,516,231 B1
(45) Date of Patent: Feb. 4, 2003

(54) ENDOCARDIAL ELECTRODE LEAD WITH MULTIPLE BRANCHES

(75) Inventor: Daniel Flammang, 10 Rue Carnot, 16000 Angouleme (FR)

(73) Assignee: Daniel Flammang, Angouleme (FR)

( * ) Notice: Subject to any disclaimer, the term of this patent is extended or adjusted under 35 U.S.C. 154(b) by 0 days.

(21) Appl. No.: 09/586,940

(22) Filed: Jun. 2, 2000

(30) Foreign Application Priority Data

Jun. 2, 1999 (DE) .......................... 199 25 853

(51) Int. Cl.⁷ ................................. A61N 1/05
(52) U.S. Cl. ........................ 607/122; 607/5; 607/127
(58) Field of Search ................... 600/373, 374, 600/375, 393, 509, 515, 519; 607/4, 5, 7, 9, 14, 15, 122, 123, 125, 126, 127

(56) References Cited

U.S. PATENT DOCUMENTS

| | | | |
|---|---|---|---|
| 3,866,615 A | | 2/1975 | Hewson |
| 4,800,883 A | * | 1/1989 | Winstrom ............... 128/419 |
| 5,439,485 A | | 8/1995 | Mar et al. ............... 607/119 |
| 5,800,465 A | * | 9/1998 | Thompson et al. ........ 607/9 |
| 5,855,592 A | | 1/1999 | McGee et al. |
| 5,935,082 A | * | 8/1999 | Albrecht et al. ........ 600/515 |
| 6,076,012 A | * | 6/2000 | Swanson et al. ......... 604/21 |

FOREIGN PATENT DOCUMENTS

| | | |
|---|---|---|
| DE | 196 26 352 | 1/1998 |
| EP | 0 281 219 | 9/1988 |
| EP | 0 426 089 | 5/1991 |
| EP | 0 479 435 | 4/1992 |
| EP | 0 522 693 | 1/1993 |
| EP | 0 538 990 | 4/1993 |
| EP | 0 574 609 | 12/1993 |
| EP | 0 601 328 | 6/1994 |
| EP | 0 601 338 | 6/1994 |
| EP | 0 602 356 | 6/1994 |
| EP | 0 646 391 | 4/1995 |
| EP | 0 648 514 | 4/1995 |
| WO | WO 92/03329 | 3/1992 |
| WO | WO 92/09329 | 6/1992 |
| WO | WO 94/03233 | 2/1994 |
| WO | WO97/36639 | 1/1997 |
| WO | WO98/11939 | 3/1998 |

* cited by examiner

*Primary Examiner*—Jeffrey R. Jastrzab
*Assistant Examiner*—Frances P. Oropeza
(74) *Attorney, Agent, or Firm*—Catherine M. Voorhees; Venable, LLP

(57) ABSTRACT

A cardioversion arrangement having an electrode arrangement for the intracardial discharge of electrical pulses in the atrium of a heart, having an electrode line and in the region of its distal end a plurality of electrodes which can be electrically connected by way of the electrode line to an electrical pulse-discharging device and a defibrillator, wherein the electrode-bearing region at the distal end of the electrode line is split into two branches of which one is in the form of a septal branch and the other is in the form of a lateral branch for assuming a septal position and a lateral position in the atrium of a heart, wherein the branches are respectively provided with electrodes in such a way that each electrode of a branch is associated in pair-wise manner with an electrode of the other branch, for the discharge of bipolar pulses, and the cardioversion arrangement is designed to record intra-atrial electrograms by means of the electrodes by receiving electrical signals between a respective two of the electrodes in the bipolar mode of operation.

31 Claims, 7 Drawing Sheets

ENDOCARDIAL ELECTRODE LEAD WITH MULTIPLE BRANCHES

BACKGROUND OF THE INVENTION

The invention concerns a cardioversion arrangement having an electrode arrangement for the intracardial discharge of electrical pulses in the atrium of a heart, having an electrode line and in the region of its distal end a plurality of electrodes which are electrically connected by way of the electrode line to an electrical pulse-discharging device such as a defibrillator or a cardioverter or antitachycardia pacer.

Certain cardiac palpitations and arrhythmia phenomena, including in particular ventricular and atrial fibrillation, but possibly also accelerating tachycardia phenomena which have not yet passed into the state of fibrillation are electrotherapeutically treated with good prospects of success by applying short-duration electrical pulses or shocks to the sensitive cardiac tissue.

In that situation, in order to rapidly achieve termination of those life-threatening arrhythmia effects with a high level of certainly, relatively high voltages are conventionally applied and high levels of energy are supplied to the cardiac tissue, which in many cases results in tissue damage and serious stresses such as pain for the patient. In addition, in relation to implantable units, the provision of those high voltages and high energy levels requires expensive apparatus implementation with special structural and insulating elements, in particular powerful batteries and capacitors. Finally, electrode arrangements of large area were and still are used for transmitting the cardioversion energy to the cardiac tissue, and the production and implantation thereof involves a high cost level.

The design of cardioverters or defibrillators (hereinafter jointly referred to by the term "cardioverter") and the associated electrode arrangements has been the subject of a drive for increasing perfection. In that respect, on the one hand numerous technical solutions have been proposed for ascertaining and providing, in the best possible differentiated fashion, the energy and voltage required for cardioversion of the specific cardiac arrhythmia phenomena involved as well as advantageous pulse shapes and sequences and on the other hand various electrode arrangements have been proposed, which were each considered advantageous from given respective points of view. In actual fact substantial practical improvements which have promoted the widespread practical use of implanted cardioverters or defibrillators and combined pacemakers/cardioverters have proven successful.

In the course of that development increasingly refined and powerful endocardiac defibrillation electrode lines have been described, which afford considerable advantages in terms of implantation and in regard to the operative risks, see for example WO/A-94/03233, EP-A 0 602 356 or the present applicants' prior application DE 196 26 352.2. The endeavours in that respect are inter alia along the lines of applying a cardioversion shock to larger areas of the cardiac tissue by the provision of a plurality of and/or large-area electrodes on an endocardiac line, and thereby approximating the area of action of endocardiac electrode arrangements to that of subcutaneous or epicardiac surface electrodes.

Further recent developments concern the combination of endocardiac electrode lines with subcutaneous or epicardiac surface electrodes—see in that respect inter alia WO-A-92/09329 and EP-A-0 522 693—or also with vessel-type electrodes, see EP-A-0 601 383.

EP-A-0 281 219 proposes the use of biphase pulses (which occur in succession in respect of time) of exponentially falling amplitude for a defibrillator. That arrangement has three ring or tip electrodes arranged on an endocardial electrode line, and a subcutaneous plate electrode, and the shock energy is coupled out by way of two outputs which are connected in various alternative forms to the electrodes. Use of the biphase pulses made it possible to achieve a reduction in the mean energy requirement for defibrillation.

EP-A-0 648 514 describes a defibrillation with a pulse generator for multi-phase shock pulses. EP-A-0 574 609 and EP-A-0 646 391 describe uses, which are refined from the point of view of improved current distribution in the heart tissue, of the principle of biphase pulses for a defibrillator having a plurality of outputs for a multiplicity of electrodes, in which the arrangement provides for timed discharge of pulses of different polarities to various electrodes.

SUMMARY OF THE INVENTION

The above-mentioned cardioversion arrangements and the other known cardioversion arrangements suffer from various disadvantages. In particular in many cases they still do not allow for reliable defibrillation which affords the patient careful treatment.

The object of the present invention is therefore that of providing a cardioversion arrangement which permits reliable defibrillation which treats the patient carefully.

In accordance with the invention that object is attained with a cardioversion arrangement of the kind set forth in the opening part of this specification, in which the electrode-bearing region at the distal end of the electrode line is split into two branches of which one is in the form of a septal branch and the other is in the form of a lateral branch for assuming a septal position and a lateral position in the atrium or the ventricle of a heart, wherein the branches are respectively provided with electrodes in such a way that each electrode of a branch is associated in pair-wise manner with an electrode of the other branch, for the discharge of bipolar pulses, and the cardioversion arrangement is designed to record intra-atrial electrograms by means of the electrodes by receiving electrical signals between each two of the electrodes in a bipolar mode of operation.

The bipolar discharge of stimulation pulses by way of a plurality of electrodes which are associated with each other in pairs in the atrium or the ventricle of a heart permits, by dividing the defibrillating or cardioverting energy in successive slides, substantially pain-free defibrillation. Insofar as the electrodes are also in the form of sensors for receiving electrical signals, the conditions of the heart can be recorded in a highly differentiated manner and the discharge of current pulses by way of the electrodes can be suitably accurately controlled.

The electrodes are preferably respectively equidistantly arranged on each of the two branches of the electrode line. Together with the paired association of the electrodes with each other, with an electrode line of that kind, the atrium or the ventricle of a heart can be surveyed or measured by virtue of recording electrical signals or stimulated by virtue of the discharge of electrical pulses, in a practically slice-like fashion. Those slices are determined by the electrodes which are associated with each other in pairs and for example can be arranged substantially parallel to each other in succession at a spacing of a centimetre.

A preferred cardioversion arrangement is one having an additional neutral electrode like the housing of an implantable defibrillator, wherein the cardioversion arrangement is designed to record intra-atrial electrograms by means of the electrodes by receiving electrical end signals between the neutral electrode and one respective electrode in the unipolar mode of operation. Such an arrangement increases the number of detectable parameters so that electrotherapy can be still more specifically matched to the symptoms or syndrome.

Cardioversion arrangements are also preferred, which are designed either alternatively or in combination for the discharge of an electrical pulse by way of the neutral electrode and one of the electrodes in the unipolar mode of operation or by way of second electrodes in the bipolar mode of operation. Cardioversion arrangements of that kind make it possible to generate greatly differentiated stimulation patterns which in addition can be very accurately matched to the symptoms or syndrome so that a therapy of fibrillations can be initiated at a very early stage and effected at the same time in a highly efficient manner while dealing gently with the patient.

In addition a cardioversion arrangement preferably has means for the discharge of stimulation pulses by way of the electrodes in the bipolar and/or unipolar mode of operation and means for subsequently recording intra-atrial electrograms by means of electrodes for receiving electrical signals between the neutral electrode and a respective one of the electrodes in the unipolar mode of operation and/or between two of the electrodes in the bipolar mode of operation. A cardioversion arrangement of that kind permits specific stimulation of the heart tissue before recording the electrograms already referred above, for determining the symptoms or syndrome. The latter can be ascertained thereby in a still more differentiated manner.

Also preferred is a cardioversion arrangement having a neutral electrode and control means which are of such a nature that at least two respective electrodes which are associated with each other in paired relationship, of the lateral and the septal branches, are actuable simultaneously for recording electrical signals between the neutral electrode and the electrodes in the unipolar mode of operation, and analysis and comparison means which are such that the electrical signals ascertained by means of an electrode in the lateral branch and an electrode in the septal branch are comparable in terms of their relative phase position or isochronicity. Further preferred embodiments of the comparison means are distinguished in that the electrical signals ascertained by means of an electrode in the lateral branch and an electrode in the septal branch are comparable in respect of their duration and/or their regularity and/or their isoelectric time duration and/or their voltage rise or fall and/or their morphology. The various alternative embodiments of the comparison means referred to permit greatly differentiated determination of the symptoms or syndrome.

Correspondingly a cardioversion arrangement which is preferred is one in which the control means are such that each of the electrodes is actuable with the electrode associated therewith in paired relationship of the other branch, in bipolar relationship, for recording electrical signals between those electrodes, while the comparison means are such that the electrical signals ascertained simultaneously by means of the pairs of mutually associated electrodes are comparable in respect of their relative phase position or isochronicity. Alternatively or in addition comparison means can be such that the electrical signals ascertained simultaneously by means of the pairs of mutually associated electrodes are comparable in respect of their duration and/on their regularity and/or their isoelectric time duration and/or their voltage rise or fall and/or in respect of their morphology.

The recordal of electrical signals both in the unipolar mode of operation between an electrode and a neutral electrode or a bipolar mode of operation between two electrodes and analysis of the signals in respect of the described parameters results in a large number of items of information which can be used to control defibrillation pulses which are possibly required.

For effectively controlling the defibrillation pulses the cardioversion arrangement preferably has a comparative pattern storage means which is connected to the analysis and comparison means and which can store comparative values for the values generated by the analysis and comparison means.

A further preferred cardioversion arrangement is distinguished by control means which are connected to the electrodes of the septal and lateral branches and which are such that the electrodes of the septal and lateral branches are actuable for discharge of a defibrillation pulse in a bipolar mode of operation. In that connection, the pulse control means are additionally preferably connected to the comparative pattern storage means and the analysis and comparison means. Particularly preferred is a cardioversion arrangement whose pulse control means are such that the electrodes of the septal branch can be actuated more strongly than the electrodes of the lateral branch or conversely.

Preferably, the pulse control means are adapted for simultaneous actuation of the electrodes of the septal and the lateral branches and the neutral electrode. Also preferred is a cardioversion arrangement which has an electrode line, which is adapted to assume a position in the ventricle, with ventricle electrodes, and the pulse control means of which are adapted for the simultaneous actuation of the electrodes of the septal and lateral branches and the ventricle electrode. In addition, the pulse control means are preferably of such a nature that the electrodes of septal and lateral branches are simultaneously actuable for the discharge of a defibrillation pulse in the bipolar mode of operation. In an alternative preferred embodiment, the pulse control means are such that the pairs of mutually associated electrodes of the septal and lateral branches are actuable successively for the discharge of a defibrillation pulse in the bipolar mode of operation. By means of the last-mentioned alternative configuration, it is particularly possible for the slices or layers defined by the electrodes of the lateral and the septal branches in the atrium of a heart to be stimulated in succession. That permits particularly effective and pain-free defibrillation.

BRIEF DESCRIPTION OF THE DRAWINGS

The invention will now be described in greater detail by means of an embodiment with reference to the accompanying drawings in which.

DETAILED DESCRIPTION OF THE DRAWINGS

Figure 1:
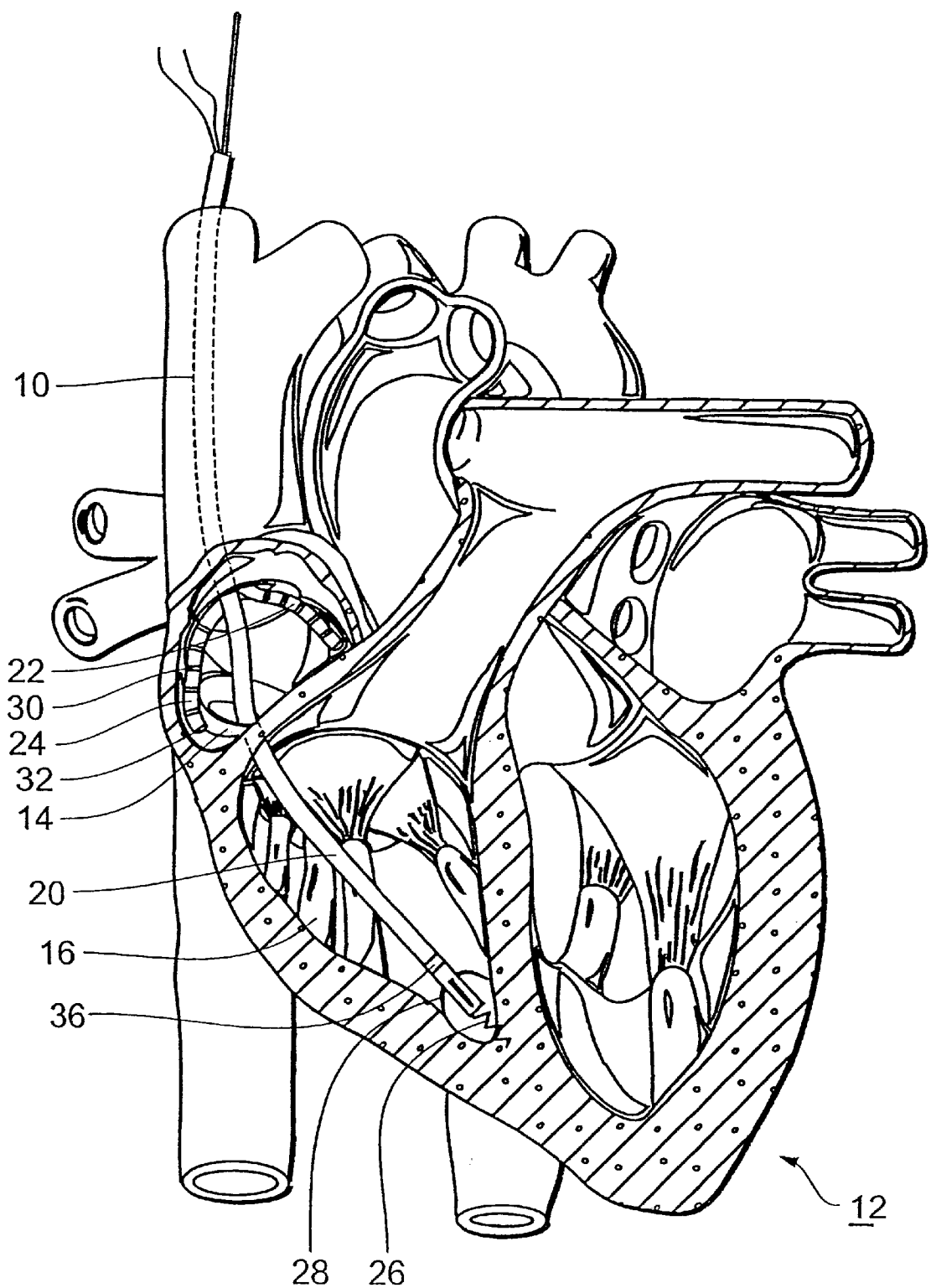
FIG. 1 shows an electrode arrangement according to the invention inserted into the atrium of a human heart.

FIG. 1 shows the distal end of an electrode line 10 in the position which it assumes in a heart 12, more precisely in the right atrium 14 thereof and in the right ventricle 16 thereof. The distal end of the electrode line 10 has three branches, a ventricular branch 20, a septal branch 22 and a lateral branch 24. The ventricular branch 20 extends into the ventricle 16 of the heart 12. The distal end of the ventricular branch 20 is fixed by way of a screwing-in tip 26 in the heart tissue (myocardium) and held at a predetermined spacing relative to the myocardium by way of spacers 28, also referred to as tines.

The septal branch 22 and the lateral branch 24 bear against the walls of the atrium 14, more specifically the septal branch 22 against the inner side of the atrium, which is towards the septum, and the lateral branch against the outer side wall of the atrium.

Figure 2A:
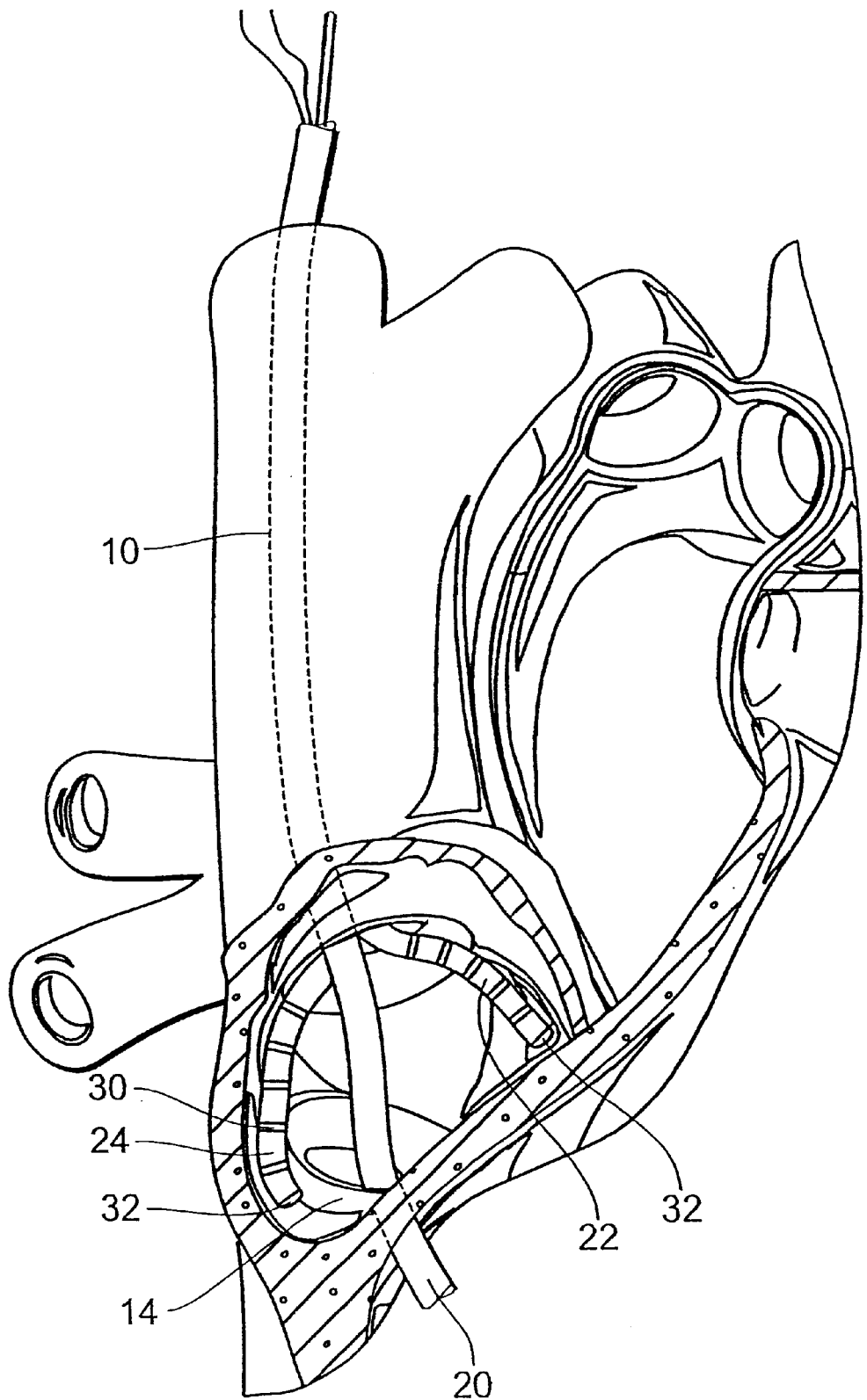
FIG. 2a is a view on an enlarged scale of a part from FIG. 1.

As can be clearly seen in particular from FIG. 2a both the lateral and also the septal branches 22 and 24 are provided with electrically conducting surface portions which serve as electrodes and which are in the form of ring electrodes 30 and tip electrodes 32. Each of the two branches 22 and 24 is provided on its last five centimetres with a total of six electrodes 30 and 32, more specifically in each case a respective tip electrode 32 and five electrodes 30 occurring in succession therefrom at respective spacings of a centimetre. The two tip electrodes 32 and the respective following ring electrodes 30 of the septal and lateral branches 22 and 24 are respectively associated with each other in pairs. In that way the electrodes 30 and 32 form respective bipoles which are arranged in substantially mutually parallel relationship and which subdivide the atrium 14 into five identical slices, each of which is one centimetre high, beginning at the transition of the upper vena cava to the right atrium and from there extending downwardly by five centimetres.

The ventricular branch 20 also carries at its end a ring electrode as a ventricle electrode 36. The electrode 36 is held substantially without contact in relation to the myocardium in the ventricle 16 by the spacers 28.

Each of the electrodes 30, 32 and 36 is connected by way of a specific control and signal line 40 to a device (not shown) for receiving electrical signals and discharging electrical voltage pulses. The arrangement also includes an adjusting wire 60 for angular adjustment of the spacers 28 and thus for adjustment of the myocardium spacing of the electrode 36. For insertion of the distal end of the electrode line 10 into the right atrium 14 on the right ventricle (heart chamber) 16, provided in the electrode line in the region of the lateral branch 24 and the septal branch 22 there are preferably memory metal structures which contain titanium and which make it possible for the septal branch 22 and the lateral branch 24, upon insertion of the electrode line, to bear quite tightly against the ventricular branch 20. By warming through the memory metal structure present in the septal branch 22 and in the lateral branch 24, it assumes a predetermined shape which causes it to bear in the septal and lateral branches 22 and 24 against the walls of the atrium 14, as shown in FIGS. 1 and 2.

Figure 2B:
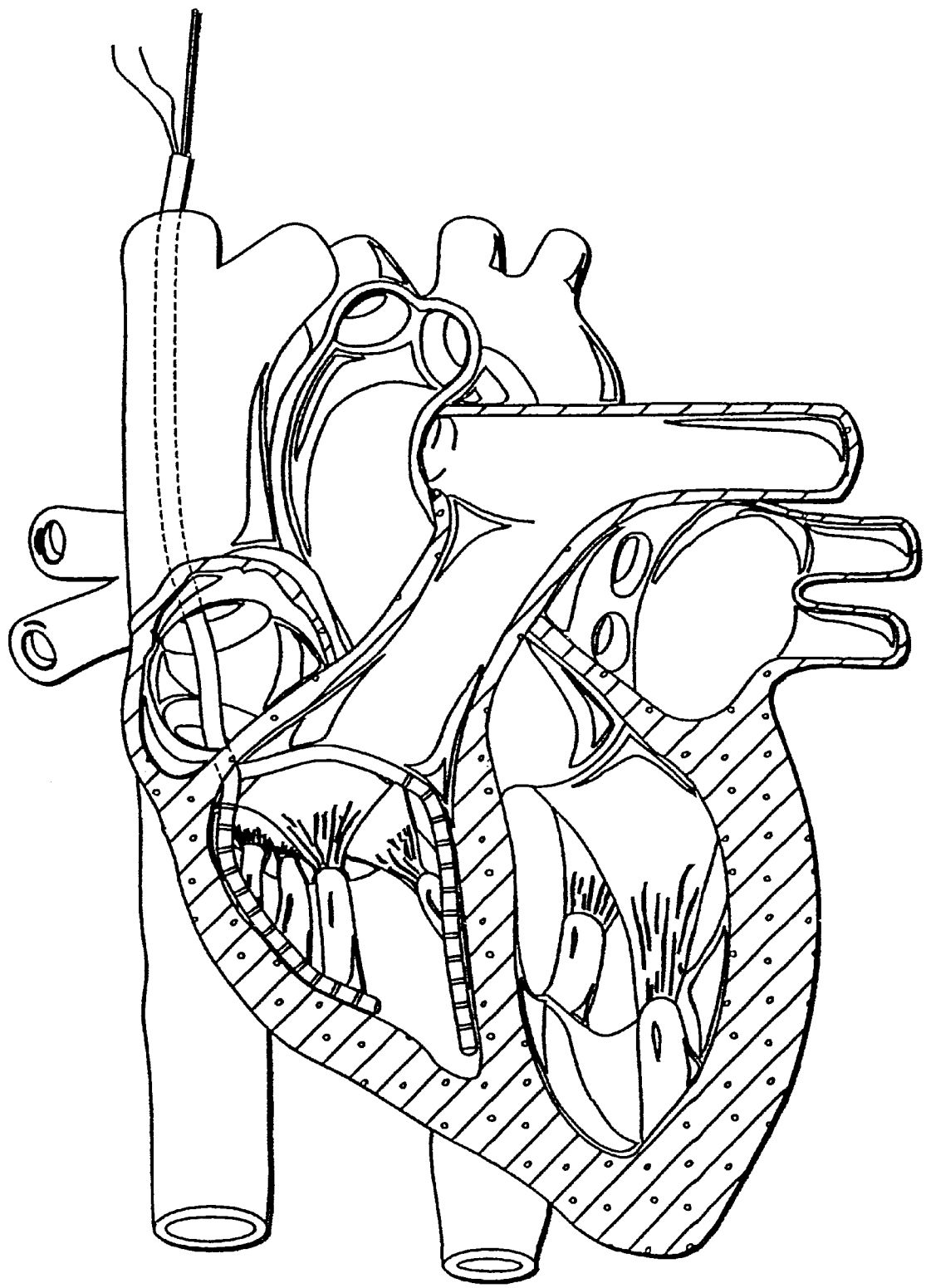
FIG. 2b shows an electrode arrangement according to the invention inserted into the ventricle of a human heart.

FIG. 2b shows an electrode arrangement similar to FIG. 2a, with the electrodes being placed within the ventricle of the heart. Two branches of the electrode line are likewise placed near the lateral wall of the right ventricle and the septum, respectively.

Figure 3:
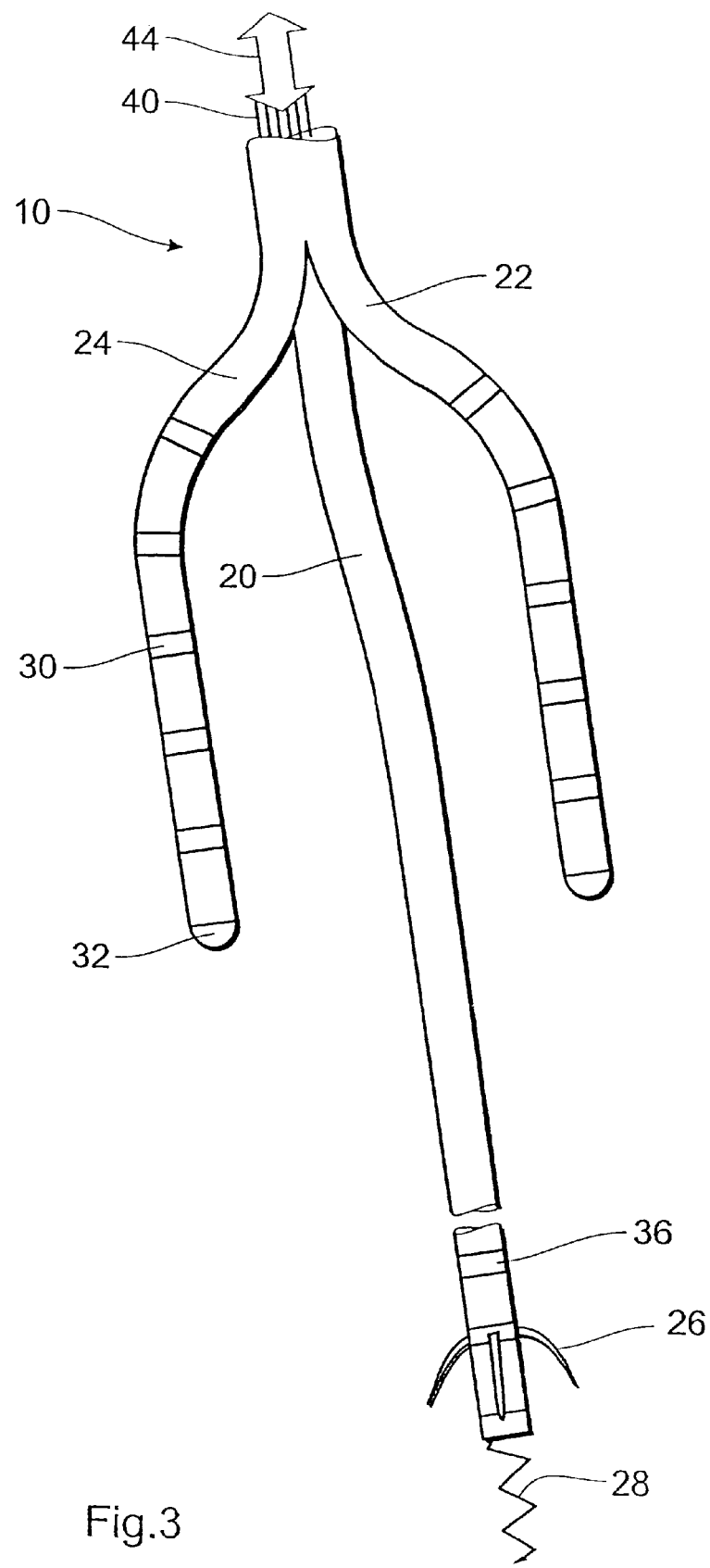
FIG. 3 is a view on an enlarged scale of the distal end of the electrode arrangement of FIG. 1.

FIG. 3 is a view on an enlarged scale of the distal end, which is illustrated in FIGS. 1 and 2, of the electrode line 10. Shown therein are the septal branch 22, the lateral branch 24 and the ventricular branch 20 with the electrodes 30, 32 and 36 arranged therein. Also shown therein are the spacers 28 and the screwing-in tip 26. The Figure also shows the signal and control lines 40 to the electrodes 30, 32 and 36 which are assembled to form a bus 44.

Figure 4:
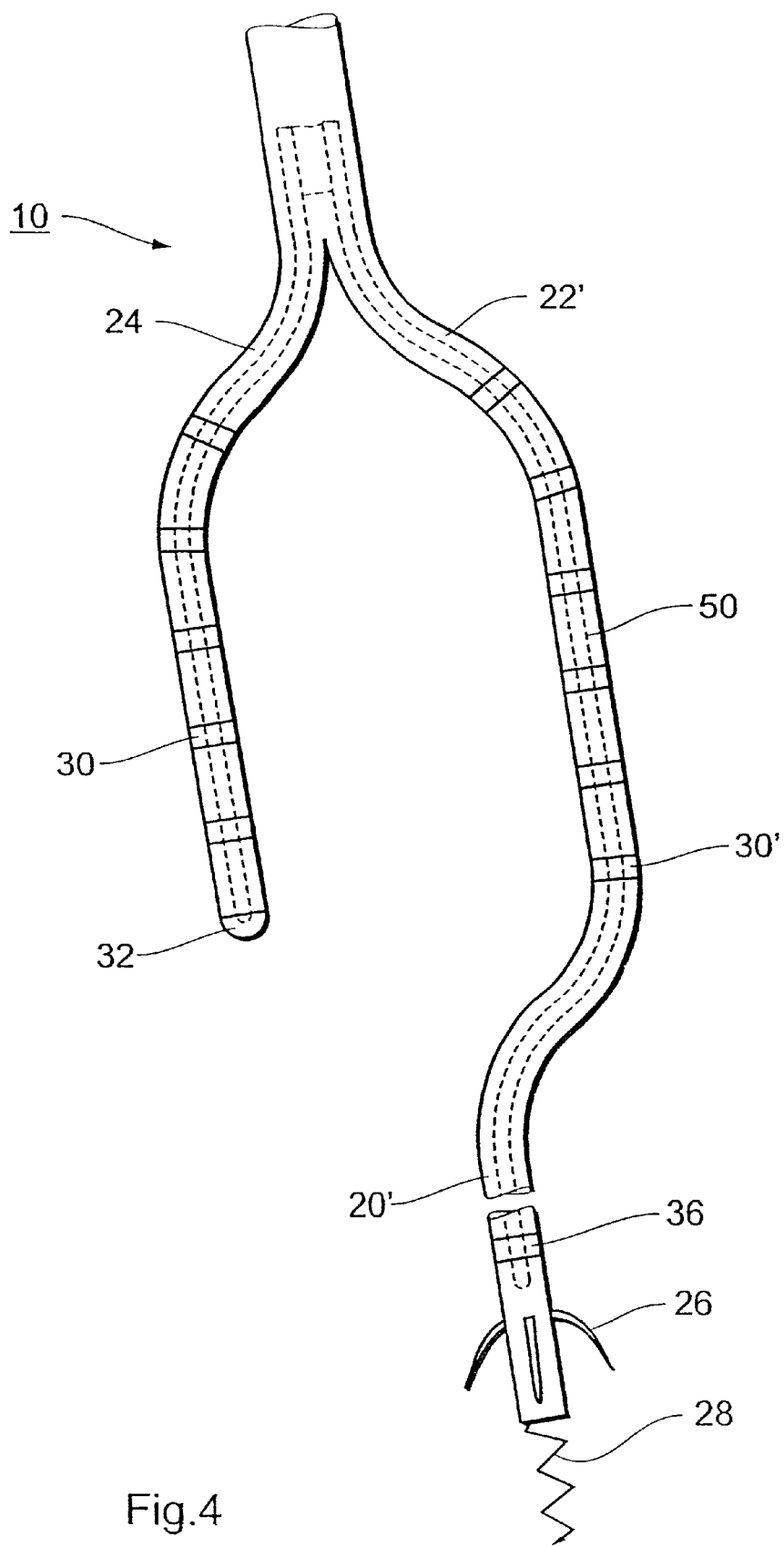
FIG. 4 shows an alternative electrode arrangement to that shown in FIG. 3.

FIG. 4 shows an alternative to the embodiment shown in FIGS. 1 and 3 of the distal end of the electrode line. In the case of the electrode line 10' illustrated in FIG. 4, the lateral branch 24 is of precisely the same nature as in FIGS. 1 to 3. The septal branch 22' however is extended and goes directly into the ventricular branch 20'. In order to achieve a similar configuration with the electrode arrangement shown in FIG. 4 to that involved in FIGS. 1 to 3, the septal branch 22', instead of a tip electrode, has a function ring electrode 30'. In other respects the arrangement of the electrodes 30' and 32' which are intended to be positioned in the atrium is substantially the same as in the arrangement shown in FIG. 3. FIG. 4 shows in broken line moreover the memory metal structure 50 which has already been referred to in connection with FIG. 3.

Figure 5:
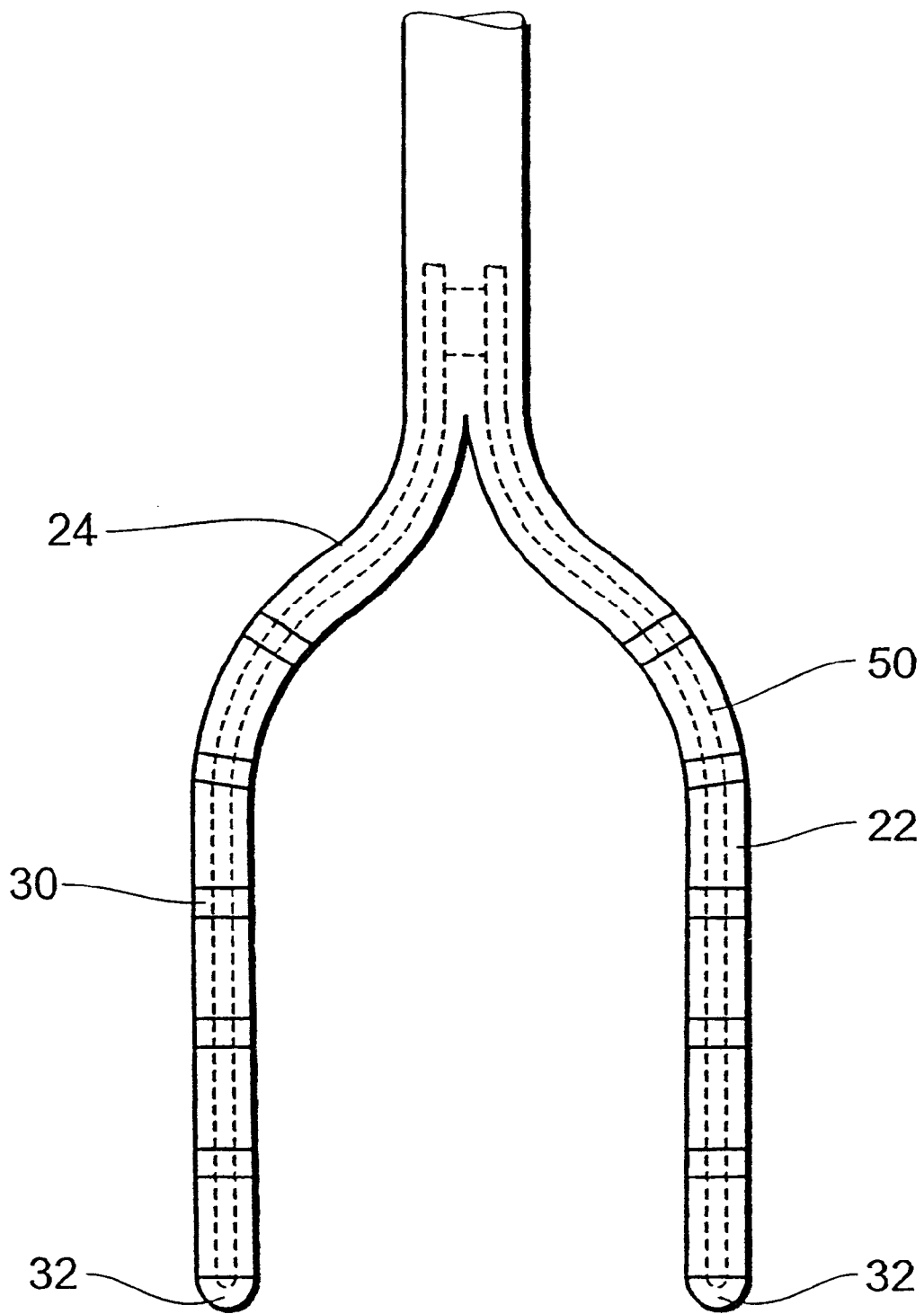
FIG. 5 shows an electrode arrangement without ventricle electrode.

FIG. 5 shows a simplified electrode line 10' which does not have a ventricular branch and which in other respects corresponds to the electrode arrangement shown in FIGS. 1 to 3.

Figure 6:
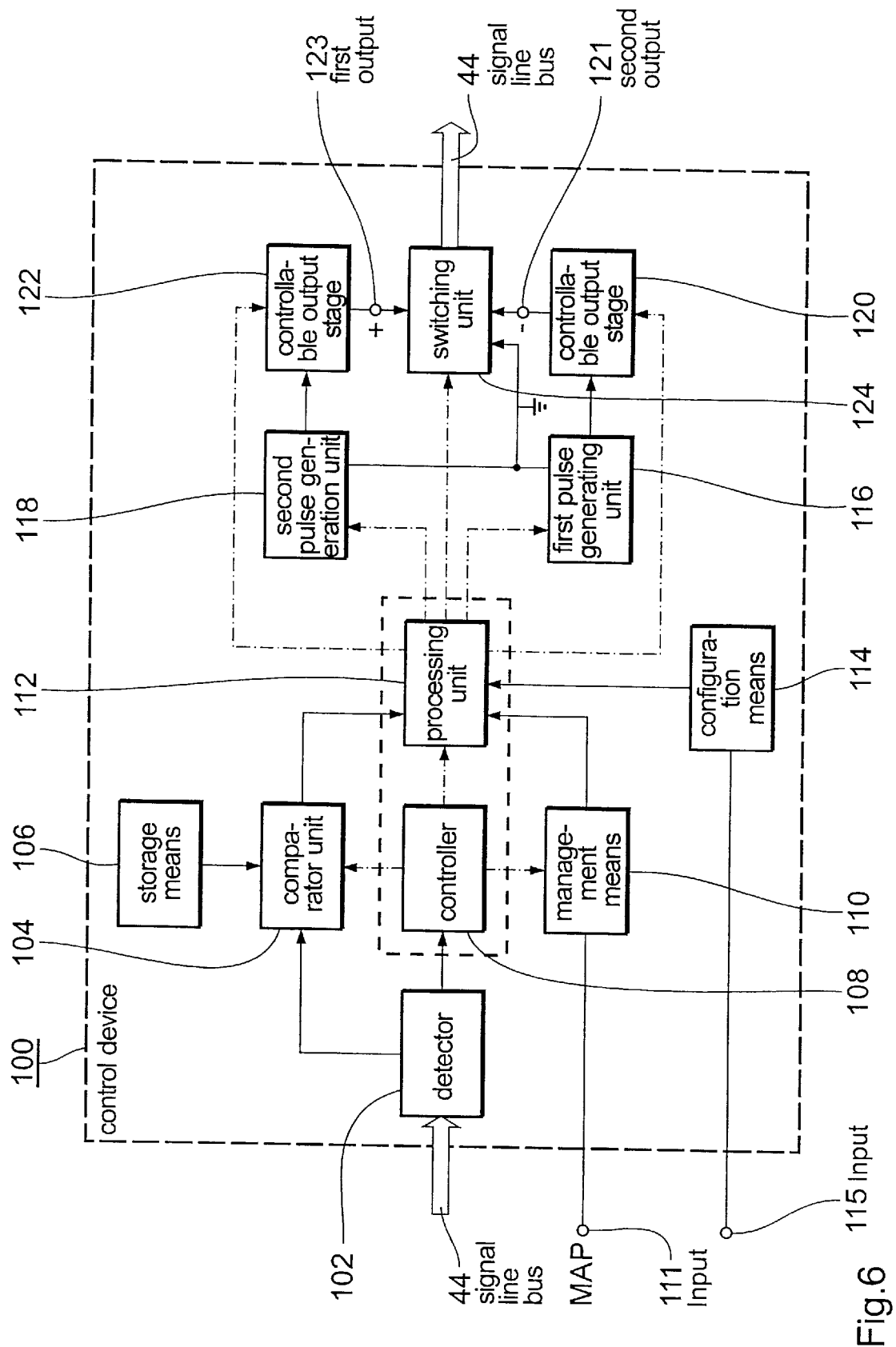
FIG. 6 shows a simplified black circuit diagram of an electrical pulse-discharging device such as a defibrillator.

FIG. 6 shows a functional, schematic circuit diagram of a device for receiving electrical signals and for discharging electrical pulses, more precisely the control device 100 thereof for control of shock pulse discharge in the case of a cardioverter with an electrode arrangement as shown in FIGS. 1 to 5.

The control device 100 is connected by way of the control and signal line bus 44 (FIG. 3) and by way of the electrode line 10 to the electrodes 30, 32 and 36. As the control and signal line bus 44 is designed bidirectionally for receiving electrical signals and for the discharge of electrical pulses, the control device 100 is connected both at its input side and also its output side to the control and signal line bus 44. Connected to the control and signal line bus 44 at the input side is a detector 102 which is connected by way of a data output to the input of an arrhythmia pattern comparator unit 104 which serves as a first comparison means and which is connected by way of a second input to an arrhythmia pattern storage means 106 as a first comparative pattern storage means. The detector 102 also has a control output by way of which it is connected to a controller 108 which at the output side is in control signal communication with the comparator unit 104, a stimulation management storage means 110 as a second comparative pattern storage means and a processing unit 112.

The stimulation management pattern storage means 110 has an input 111 with which the result of imaging detection of the specific stimulation management structures of the heart of the patient (mapping) is stored and it is connected at the output side to the processing unit 112 which transmits the storage content upon receiving a transfer signal from the controller 108.

An arrhythmia classification signal which is outputted by the comparator unit 104 is also passed to the processing unit 112, as well as data stored previously (by way of the input 115) in an electrode configuration storage means 114 for the specific electrode configuration, and the current cardioversion data which are associated with the arrhythmia classification signal. The functional units 108 and 112 are preferably in the form of microcomputers, which is symbolically represented by the broken line jointly surrounding them.

By means of the above-described apparatus, the various signals can be obtained by bipolar actuation in paired relationship of the electrodes or by actuation of an electrode together with the neutral electrode in a unipolar mode of operation with or without preceding discharge of stimulation pulses to the myocardium, and compared with each other and with the stored comparative patterns. On the basis of the comparison of those values with stored comparative values, the controller 112 derives control signals for pulse discharge. Insofar as the control arrangement has been described hitherto, it is capable of analysing the atrial electrograms recorded in unipolar or bipolar mode, centimetre by centimetre, from the sinus node region to the coronary sinus region. In that situation, each unipolar atrial electrogram of the lateral branch 24 is compared to the corresponding septal unipolar atrial electrogram in respect of isochronicity, duration, regularity, electrical time duration of the voltage rise or fall and optionally morphology. The same analysis is implemented by the electrodes which are associated with each other in pairs, bipole by bipole (or also slice by slice of the above-mentioned slices), and compared to the sinus node pattern.

After implementation of the analysis operation the processing unit 112 appropriately controls a first and second pulse generating unit 116, 118 and controllable output stage 120 connected to the first pulse generating unit 116, as well as a controllable output stage 122 connected to the second pulse generating unit 11 8, in such a way that a first voltage pulse of predetermined amplitude of negative polarity is provided at a first cardioversion output 121 and a second voltage pulse of positive polarity is produced at a second cardioversion pulse output 123, in each case in relation to apparatus ground. In addition the processing unit 112 is connected by way of a control output to a switching unit 124 which connects the ground as the voltage reference point and the outputs 121 and 123 by way of suitable electrode connections in accordance with the processing result to selected ones of the electrodes available in the arrangement, by way of the control and signal line bus 44. In that way, a shock pulse field with a level of intensity which is above the cardioversion threshold is produced in accordance with the patient-specific stimulation management structure and the current fibrillation result specifically in a predetermined region of the myocardium, while at the same time the influence on the rest of the heart tissue is minimised. In more specific terms a very slight shock is discharged for defibrillation purposes in the atrium between:

the septal and lateral branches 22 and 24, either distributed uniformly to both branches or not, both branches simultaneously and the defibrillator housing, both branches simultaneously and the ventricular branch, both branches simultaneously, the ventricular branch and the defibrillator housing.

The total amount of energy discharged can also be divided by the number of atrial myocardial slices formed by the electrode arrangement and can either be discharged simultaneously in a bipolar mode to each of the slices or can be discharged successively to the bipolar slices in a cascadelike procedure in time-delayed relationship with each other.

Control device 100 is preferably adapted to detect and to classify premature contractions, tachycardias and/or atrial or ventricular fibrillation or both.

Control device 100, in particular processing unit 112 is adapted to provide different atrial or ventricular pulse characteristics during regular pacing, after an atrial cardioversion or after an atrial premature contraction. It should be noted, that the pulse characteristics described hereinafter can be applied dependently or independently from the state of the heart detected by the control device 100. However, the combinations described below represent preferred adaptions of the control device 100, assigning various specific pulse characteristics to specific states of the heart.

In the case of a slow and stable sinus rate, for example if negative chronotropic drugs like anti-arrhythmics are used, the system should pace the twelve atrial poles formed by the electrodes simultaneously with a normal amount of energy, for example 2.5 V and 0.5 ms pulse width.

Other pacing-sensing configurations are:

To pace and to sense alternately slice by slice. In particular bipolar pacing pulses delivered to the electrodes forming the first, the third and the fifth slice, whereas sensing is done using the electrodes forming the second and the fourth slice, to pace on four slices, for instance the first four slices seen from the superior vena cava and to sense on the fifth slice.

to analyze the evoked potential after each atrial paced beat on one atrial slice and to use Logos autothreshold algorithm.

After an atrial cardioversion, the atrial pacing should be performed immediately at 80 beats per minute on the twelve poles simultaneously with pulses having a voltage of $\geq 5.0$ V and a pulse width of $\geq 1.0$ ms in order to deeply depolarize the maximum amount of atrial tissue to reset simultaneously all the atrial refractory periods. In addition to atrial pacing after an atrial cardioversion the ventricle could be paced as well, resulting in a DDD-mode stimulation. Accordingly, a device adapted to be operated in DDD-mode is preferred.

The device is preferably adapted to detect an atrial premature contraction. As soon as an atrial premature contraction has been detected by one or more of the twelve poles, the system paces immediately and simultaneously all the twelve poles with a maximum energy, that is a voltage $\geq 5.0$ V and a pulse width $\geq 1.0$ ms.

The device is preferably adapted to detect an atrial fibrillation. For treating an atrial fibrillation, there are several preferable sequences for cardioverting the atria.

Those preferred sequences include a cascade of microshocks delivered from the upper atrial slice to the lower atrial slice or a simultaneous delivery of divided microshocks energy in five slices with, for each slice, the cathode positioned on the intra-atrial septum and the anode on the lateral wall of the right atrium. This sequence is preferably repeated, for example three times.

An alternative sequence comprises a cascade or a simultaneous delivery of divided microshocks energy between each slice, each slice being formed by two opposite poles, considered as a unipolar cathode and the pacemaker housing considered as a unipolar anode. This sequence is preferably repeated several times, for instance three times.

Another preferred sequence comprises the delivery of energy diagonally between the poles of the two hemi-leads, in cascade or simultaneously. So, in this embodiment, the negative pole or electrode 1 of the septal hemi-lead could be electrically connected to the positive pole 6 of the lateral hemi-lead, septal pole 2 with the lateral pole 5, septal pole 3 with a lateral pole 5, septal pole 3 with a lateral pole 4 and so on. This sequence is preferably repeated several times, for instance three times.

Yet another sequence comprises the delivery of energy simultaneously on all twelve electrodes of both hemi-leads by using a random order for the sequence of depolarization and for the electric sign of each electrode, as far as six of the twelve electrodes are positive and the other six negative. There are also preferably several attempts provided.

If all the mentioned sequences should not provide for successful cardioversion, the control device 100 will trigger the delivery of a cardioversion shock of stronger energy, for example ≧5 Joules. This kind of cardioversion should be delivered under control of a physician, in a monitored environment and after superficial neurologic sedation.

In all cases, the total amount of delivered energy should be as low as possible, preferably lower than 1.0 Joules for a complete sequence, the sum of the energy being delivered of over different slices.

The control device 100 is also capable to allow for a single chamber VVI pacing or for dual chamber DDD/R pacing.

In addition, the control device 100 is adapted to provide for the following:

For defining the sinus rhythm, the direction and the conduction time of the sinus depolarization should keep being stable all around the clock.

As soon as atrial fibrillation is recognized in two or more of the twelve electrodes, the low splitted-energy cardioversion should be delivered according to one of sequences described beforehand.

As soon as an atrial fibrillation is recognized in two ore more of the twelve electrodes, the low splitted-energy cardioversion should be delivered according to one of the sequences described beforehand.

Control device 100 is also adapted to detect atrial flutter and atrial tachycardia by sensing fast and regular heart cycles at more than 180 beats per minute. In such instance, control device 100 is adapted to deliver treatment sequences including an atrial overdriving, that is, delivery of pacing pulses with a rate being thirty beats per minute faster than the detected tachycardia, a very fast burst for n seconds, and a cardioversion with splitted energy as described beforehand depending with a detected flutter or atrial tachycardia is stable or has degenerated into atrial fibrillation.

In combination with a splitted lead electrode being placed in the ventricle of the heart, the control device 100 will deliver similar therapies to the ventricle as they are described above for the atrium.

Alternative embodiments of the control device 100 are adapted to provide for just one or a few of the stimulation sequences described above. The sequences delivered can be coupled by means of the processing unit 112 to certain output states of the detector 102 or to the analysis described above or they may be delivered independently therefrom. However, a device having coupled specific stimulation sequences coupled to specific detection states is preferred.

It shall be noted that there are different embodiments of the cardioverter/defibrillator according to the invention, among them less complex embodiments, which are adapted carry out just one or a few of the modes or therapies being described above.

Overall the described apparatus permits highly effective and very substantially pain-free defibrillation on the basis of optimised signal analysis and pulse discharge options.

I claim:

1. A cardioversion arrangement comprising:

an electrode arrangement for the endocardial discharge of electrical pulses in an atrium or a ventricle of a heart, said electrode arrangement having an electrode line with a distal end and a plurality of electrodes disposed in the region of the distal end, which can be electrically connected by way of the electrode line to an electrical pulse-discharging device wherein the distal end of the electrode line is split into two branches and the plurality of electrodes are split between the two branches, one of the two branches is in the form of a septal branch and the other is in the form of a lateral branch for respectively assuming a septal position and a lateral position in the atrium or the ventricle of the heart; and control means for actuating an electrode from the septal branch and a respective electrode of the lateral branch such that each electrode of a branch is associated in a pair-wise manner with an electrode of the other branch and is actuated one of simultaneously and in a cascade fashion with its respective, paired electrode for bipolar discharge of stimulation electrical pulses, wherein the cardioversion arrangement is designed to record intra-atrial electrograms by receiving electrical signals between the paired electrodes of the plurality of electrodes in the bipolar mode of operation.

2. The cardioversion arrangement according to claim 1, wherein the electrodes of each branch are arranged equidistantly on the respective branch.

3. The cardioversion arrangement according to claim 1, further comprising an additional neutral electrode wherein the cardioversion arrangement is designed for recording the intra-atrial electrograms by means of receiving electrical signals between the neutral electrode and a respective one of the electrodes in a unipolar mode of operation.

4. The cardioversion arrangement according to claim 3, wherein the neutral electrode is a housing of an implantable electrical pulse-discharging device.

5. The cardioversion arrangement according to claim 3, wherein the discharge of electrical pulse occurs by way of the neutral electrode and one of the electrodes in the unipolar mode of operation.

6. The cardioversion arrangement according to claim 3, wherein at least two respective electrodes associated with each other in paired relationship of the lateral and septal branch are actuable simultaneously by the control means for receiving the electrical signals between the neutral electrode and the respective one of the electrodes in the unipolar modes of operation, and further comprising comparison means for comparing the electrical signals ascertained by means of an electrode in the lateral branch and an electrode in the septal branch with respect to their relative phase position or isochronicity.

7. The cardioversion arrangement according to claim 6, wherein the comparison means are such that the electrical signals ascertained by means of an electrode in the lateral branch and an electrode in the septal branch can be compared with respect to their duration.

8. The cardioversion arrangement according to claim 7, wherein the comparison means compare the electrical signals ascertained by means of an electrode in the lateral branch and an electrode in the septal branch with respect to their regularity.

9. The cardioversion arrangement according to claim 6, wherein the comparison means compare the electrical signals ascertained by means of an electrode in the lateral branch and an electrode in the septal branch with respect to their isoelectric time duration.

10. The cardioversion arrangement according to claim 6, wherein the comparison means compare the electrical signals ascertained by means of an electrode in the lateral branch and an electrode in the septal branch with respect to their voltage rise or fall.

11. The cardioversion arrangement according to claim 6, wherein the comparison means compare the electrical signals ascertained by means of an electrode in the lateral branch and an electrode in the septal branch with respect to their morphology.

12. The cardioversion arrangement according to claim 1, wherein the control means simultaneously actuates the paired electrodes in bipolar fashion for receiving electrical signals between said electrodes, and further comprising comparison means for comparing the electrical signals ascertained simultaneously by means of the pairs of mutually associated electrodes with respect to their relative phase position or isochronicity.

13. The cardioversion arrangement according to claim 12, wherein the comparison means compare the electrical signals ascertained simultaneously by means of the pairs of mutually associated electrodes with respect to their duration.

14. The cardioversion arrangement according to claim 12, wherein the comparison means compare the electrical signals ascertained simultaneously by means of the pairs of mutually associated electrodes with respect to their regularity.

15. The cardioversion arrangement according to claim 12, wherein the comparison means compare the electrical signals ascertained simultaneously by means of the pairs of mutually associated electrodes with respect to their isoelectric time duration.

16. The cardioversion arrangement according to claim 12, wherein the comparison means compare the electrical signals ascertained simultaneously by means of the pairs of mutually associated electrodes with respect to their voltage rise or fall.

17. The cardioversion arrangement according to claim 12, wherein the comparison means compare the electrical signals ascertained simultaneously by means of the pairs of mutually associated electrodes with respect to their morphology.

18. The cardioversion arrangement according to claim 1, further comprising means for analyzing and comparing electrical signals received from the electrode line and a comparative pattern storage means, which is connected to the analysis and comparison means, for storing comparative values generated by the analysis and comparison means.

19. The cardioversion arrangement according to claim 1, further comprising pulse control means, which are connected to the electrodes of the septal and lateral branches, and for actuating the electrodes of the septal and lateral branches for the discharge of a defibrillation pulse in the bipolar mode of operation.

20. The cardioversion arrangement according to claim 19, wherein the pulse control means actuate the electrodes of the septal branch more strongly than the electrodes of the lateral branch.

21. A cardioversion arrangement according to claim 19, further comprising a neutral electrode, wherein the pulse control means are designed for simultaneous actuation of the electrodes of the septal and the lateral branches and the neutral electrode.

22. The cardioversion arrangement according to claim 18 or claim 19, wherein the electrode line is adapted to assume a position in the ventricle of the heart and has a ventricle electrode, and wherein the pulse control means are adapted for the simultaneous actuation of the septal and the lateral branches and the ventricle electrode.

23. The cardioversion arrangement according to claim 19, wherein the pulse control means simultaneously actuate the paired electrodes of the septal and the lateral branches for discharge of the defibrillation pulse in the bipolar mode of operation.

24. The cardioversion arrangement according to successively actuate claim 19, wherein the pulse control means successively actuate pairs of mutually associated electrodes of the septal and lateral branches in a cascade like fashion for discharge of the defibrillation pulse in the bipolar mode of operation.

25. The cardioversion arrangement according to claim 1, further comprising means for distributing the discharge of stimulation electrical pulses uniformly between the septal branch and the lateral branch.

26. The cardioversion arrangement according to claim 4, further comprising means for distributing the discharge of stimulation electrical pulses between the septal branch and the lateral branch simultaneously and the housing of the implantable electrical pulse-discharging device, the implantable electrical pulse-discharging device being a defibrillator.

27. The cardioversion arrangement according to claim 4, wherein the electrode line is adapted to assume a position in a ventricle of the heart and has a ventricular branch with a distal end and a ventricle electrode at the ventricular branch distal end, the implantable electrical pulse-discharging device being a defibrillator, and further comprising means for distributing the discharge of stimulation electrical pulses between the septal branch and the lateral branch simultaneously, the ventricular branch and the housing of the defibrillator.

28. A cardioversion arrangement comprising:
an electrode arrangement for the endocardial discharge of electrical pulses in an atrium or a ventricle of a heart, said electrode arrangement having an electrode line with a distal end and a plurality of electrodes disposed in the region of the distal end, which can be electrically connected by way of the electrode line to an electrical pulse-discharging device wherein the distal end of the electrode line is split into two branches and the plurality of electrodes are split between the two branches, one of the two branches is in the form of a septal branch and the other is in the form of a lateral branch for respectively assuming a septal position and a lateral position in the atrium or the ventricle of the heart; and control means for actuating an electrode from the septal branch and a respective electrode of the lateral branch such that each electrode of a branch is associated in a pair-wise manner with an electrode of the other branch and is actuated one of simultaneously and in a cascade fashion with its respective, paired electrode for bipolar discharge of stimulation electrical pulses, wherein the cardioversion arrangement is designed to record intra-atrial electrograms by receiving electrical signals between the paired electrodes of the plurality of electrodes in the bipolar mode of operation, wherein the septal and lateral branches each have five electrodes disposed thereon and at respective spacings on each branch so that electrodes at the same spacing are paired for the bipolar discharge of stimulation electrical pulses and the paired electrodes form respective bipoles that are arranged in substantially mutually parallel relationship and subdivide the atrium or ventricle of the heart into five substantially identical slices, and wherein the control means actuates the paired electrodes alternately slice by slice so that bipolar pacing pulses are delivered to the electrodes forming the first, third and fifth slices and sensing of electrical pulses is done using the electrodes forming the second and the fourth slices.

29. A cardioversion arrangement comprising:
an electrode arrangement for the endocardial discharge of electrical pulses in an atrium or a ventricle of a heart, said electrode arrangement having an electrode line with a distal end and a plurality of electrodes disposed in the region of the distal end, which can be electrically connected by way of the electrode line to an electrical pulse-discharging device wherein the distal end of the electrode line is split into two branches and the plurality of electrodes are split between the two branches, one of the two branches is in the form of a septal branch and the other is in the form of a lateral branch for respectively assuming a septal position and a lateral position in the atrium or the ventricle of the heart; and control means for actuating an electrode from the septal branch and a respective electrode of the lateral branch such that each electrode of a branch is associated in a pair-wise manner with an electrode of the other branch and is actuated one of simultaneously and in a cascade fashion with its respective, paired electrode for bipolar discharge of stimulation electrical pulses, wherein the cardioversion arrangement is designed to record intra-atrial electrograms by receiving electrical signals between the paired electrodes of the plurality of electrodes in the bipolar mode of operation, wherein the septal and lateral branches each have five electrodes disposed thereon and at respective spacings on each branch so that electrodes at the same spacing are paired for the bipolar discharge of stimulation electrical pulses and the paired electrodes form respective bipoles that are arranged in substantially mutually parallel relationship and subdivide the atrium is or ventricle of the heart into five substantially identical slices, and wherein the control means actuates the paired electrodes alternately slice by slice so that bipolar pacing pulses are delivered to the electrodes forming the first through fourth slices seen from a superior vena cavity of the heart and the electrodes of the fifth slice sense the electrical pulses.

30. The cardioversion arrangement according to claim 1 for the treatment of atrial fibrillation, wherein the septal and lateral branches each have a number of electrodes disposed thereon and at respective spacing on each branch so that electrodes at the same spacing are paired for the bipolar discharge of stimulation electrical pulses and the paired electrodes form respective bipoles that are arranged in substantially mutually parallel relationship and subdivide the atrium of the heart into a number of substantially identical slices having an upper atrial slice and a lower atrial slice, and wherein the control means actuates the paired electrodes slice by slice in a cascade fashion so that a cascade of microshocks are delivered from the electrodes forming the upper atrial slice down to the electrodes forming the lower atrial slice.

31. The cardioversion arrangement according to claim 1, wherein the septal and lateral branches each have five electrodes disposed thereon and at respective spacings on each branch so that electrodes at the same spacing are paired for the bipolar discharge of stimulation electrical pulses and the paired electrodes form respective bipoles that are arranged in substantially mutually parallel relationship and subdivide the atrium of the heart into five substantially identical slices, and wherein the control means actuate the paired electrodes slice by slice so that bipolar pacing pulses are simultaneously delivered to the electrodes forming the five slices.

* * * * *